United States Patent
Ripoll et al.

(10) Patent No.: US 9,234,858 B2
(45) Date of Patent: Jan. 12, 2016

(54) DEVICE AND METHOD FOR ESTIMATING THE RESISTANCE OF THE GROUND CONNECTION FOR AN ELECTRICAL APPARATUS

(75) Inventors: Christophe Ripoll, Chevreuse (FR); Pascal Caumon, Rambouillet (FR)

(73) Assignee: RENAULT s.a.s., Boulogne-Billancourt (FR)

( * ) Notice: Subject to any disclaimer, the term of this patent is extended or adjusted under 35 U.S.C. 154(b) by 171 days.

(21) Appl. No.: 14/118,665

(22) PCT Filed: May 14, 2012

(86) PCT No.: PCT/FR2012/051072
§ 371 (c)(1),
(2), (4) Date: Mar. 6, 2014

(87) PCT Pub. No.: WO2012/156635
PCT Pub. Date: Nov. 22, 2012

(65) Prior Publication Data
US 2014/0176163 A1    Jun. 26, 2014

Related U.S. Application Data

(60) Provisional application No. 61/489,716, filed on May 25, 2011.

(30) Foreign Application Priority Data

May 19, 2011   (FR) .................................... 11 54382

(51) Int. Cl.
*G01N 27/04*    (2006.01)
*G01R 27/20*    (2006.01)
(Continued)

(52) U.S. Cl.
CPC . *G01N 27/04* (2013.01); *B60L 3/00* (2013.01); *B60L 11/1816* (2013.01); *B60L 11/1818* (2013.01); *G01R 27/20* (2013.01); *B60L 2230/12* (2013.01); *G01R 31/025* (2013.01); *Y02T 10/7005* (2013.01); *Y02T 10/7088* (2013.01); *Y02T 90/121* (2013.01); *Y02T 90/14* (2013.01)

(58) Field of Classification Search
CPC ....... G01N 27/04; G01R 27/20; G01R 31/025
See application file for complete search history.

(56) References Cited

U.S. PATENT DOCUMENTS

| | | | |
|---|---|---|---|
| 1,775,686 A * | 9/1930 | Milnor | G01R 27/18 324/509 |
| 6,745,146 B1 * | 6/2004 | Brown | G01R 31/025 702/119 |

(Continued)

FOREIGN PATENT DOCUMENTS

| | | |
|---|---|---|
| EP | 0 864 873 | 9/1998 |
| EP | 0 915 347 | 5/1999 |

(Continued)

OTHER PUBLICATIONS

International Search Report Issued Aug. 27, 2012 in PCT/FR12/051072 Filed May 14, 2012.

(Continued)

*Primary Examiner* — Jermele M Hollington
(74) *Attorney, Agent, or Firm* — Oblon, McClelland, Maier & Neustadt, L.L.P.

(57) ABSTRACT

A device and method for estimating resistance of a ground connection of an electrical apparatus connected to an electrical power network, also connected to ground by an additional resistance, and including at least one impedance disposed at an input of the electrical apparatus, a voltage generator connected to the impedance and connected to ground, a mechanism to measure current flowing to ground, and a calculation mechanism to estimate the resistance of the ground connection as a function of the current flowing to ground. The device and method can for example find application in estimation of resistance of a ground connection of a charger of an electric or hybrid traction motor vehicle.

14 Claims, 2 Drawing Sheets

(51) Int. Cl.
  *B60L 3/00* (2006.01)
  *B60L 11/18* (2006.01)
  *G01R 31/02* (2006.01)

(56) References Cited

U.S. PATENT DOCUMENTS

2006/0144165 A1* 7/2006 Pietsch .................. G01R 27/14
                                                              73/862.045
2015/0198644 A1* 7/2015 Ripoll .................... G01R 27/20
                                                              324/722

FOREIGN PATENT DOCUMENTS

GB          2 191 591         12/1987
JP          2001 242206        9/2001

OTHER PUBLICATIONS

French Search Report Issued Jan. 18, 2012 in FR 1154382 Filed May 19, 2011.
U.S. Appl. No. 14/401,436, filed Nov. 14, 2014, Merienne.

* cited by examiner

DEVICE AND METHOD FOR ESTIMATING THE RESISTANCE OF THE GROUND CONNECTION FOR AN ELECTRICAL APPARATUS

The invention relates to the ground connection for electrical apparatuses and more particularly to the estimation of the resistance of the ground connection for these apparatuses.

When some electrical apparatuses are connected to a power supply system, a leakage current that is intended to be redirected to the ground can appear. By way of example, the battery chargers for electric or hybrid traction motor vehicles are not insulated and can, when connected to a power supply system, cause a leakage current to appear.

The leakage current can cause a touch current to appear on the electrical chassis of the apparatuses if the ground connection is broken or if the resistance of the ground connection is too high. This touch current is dangerous for a user coming into contact with the electrical chassis of the apparatus in the event of the resistance of the ground connection being too high and if the passage of the current through the user is facilitated.

It is therefore necessary to estimate the resistance of the ground connection before authorizing the use of the electrical apparatus at the nominal power corresponding to the generation of high leakage currents. The expression "ground quality" will also be used. A good-quality connection has a low resistance, for example.

The aim of the invention is therefore to provide an estimate of the resistance of the ground connection for an electrical apparatus.

According to one aspect, provision is made for a device for estimating the resistance of the ground connection for an electrical apparatus when said electrical apparatus is connected to a power supply system and also connected to the ground by an additional resistance, said electrical apparatus having at least one input impedance, said estimating device being characterized in that it comprises a voltage generator having means for connecting to said input impedance and means for connecting to said ground connection, means for measuring the current flowing to the ground through said resistance of the ground connection when said means for connecting to said input impedance and to said ground connection are activated, and calculating means capable of obtaining an order of magnitude for the resistance of the ground connection, as a function of said current flowing to the ground, with respect to the value of said additional resistance.

The impedance may be a capacitance arranged at the input of the electrical apparatus or else the input impedance of a filter arranged at the input of the electrical apparatus. A prior estimate of this input impedance makes it possible to determine the current injected by the voltage generator, which is why the injected current is a function of the ground connection resistance.

The additional resistance and the resistance of the ground connection are connected in parallel. This additional resistance can notably be another object in contact with the electrical apparatus and itself connected to the ground. This additional resistance differs from the ground connection resistance. It is a priori unwanted.

The voltage generator makes it possible to cause a current to flow through the resistance of the ground connection, in order to measure the current flowing to the ground and to estimate the resistance of the ground connection. The connection of this voltage generator to the impedance is particularly advantageous and also makes it possible to cause a current to flow through the resistance of the ground connection and to loop it back in the phases of the connection to the electrical system, the impedance being connected to the various phases.

The device may furthermore comprise means for measuring the leakage current from the differential supply current for said electrical apparatus, and the calculating means may be capable of estimating the additional resistance as a function of the leakage current and of the current flowing to the ground.

The difference between the leakage currents and the currents flowing to the ground makes it possible to obtain the current flowing in the additional resistance.

The estimation of the two resistances, the resistance of the ground connection and the additional resistance, makes it possible to determine the path that the current will take. In the event of another object connected to the ground being in contact with the electrical apparatus, if the ground connection is of poor quality then the current will flow through the additional resistance of the other object.

The calculating means can comprise a table having resistance values for the ground connection, values of additional resistance and values of current flowing to the ground corresponding to said resistance values for the ground connection and to said values of additional resistance.

Thus, these tabulated values make it possible to obtain an estimate of the quality of the ground connection by means of resistance estimates. These tabulated values can be obtained by using a prior calibration step.

Furthermore, the impedance can be the input impedance of an electromagnetic compatibility filter. The voltage generator is therefore connected to the input impedance of this electromagnetic compatibility filter.

It is thus possible to use the components of this filter to charge the voltage source and to cause a current to flow through the resistance of the ground connection looping back toward the phases, for example through common-mode capacitances of an electromagnetic compatibility filter. The use of the components that are already present inside the filter makes it possible to reduce the cost of the device.

Advantageously, the voltage generator is a voltage-controlled oscillator. It is thus possible to choose a frequency enabling the current to flow in a lower-impedance path between the filter and the system. The measurement of the leakage current is thus always a function of the resistance of the ground connection.

The device may comprise means for prohibiting the use of the electrical apparatus as a function of the estimate of the resistance of the ground connection.

If the ground connection is of poor quality then the use of the electrical apparatus can be prohibited in order to protect a user.

Advantageously, the electrical apparatus may be a battery charger for an electric or hybrid traction motor vehicle.

It is thus possible to estimate the resistance of the ground connection for this charger, as well as the additional resistance, for example that of a hydraulic ramp arranged under the electric motor vehicle.

According to another aspect, provision is made for a method for estimating the resistance of the ground connection for an electrical apparatus when said electrical apparatus is connected to a power supply system and also connected to the ground by an additional resistance.

According to a general feature of the method, a current is generated between an input impedance of the electrical apparatus and the resistance of the ground connection, and the current flowing to the ground through said resistance of the ground connection is measured in order to obtain an order of magnitude for the resistance of the ground connection with respect to the value of said additional resistance.

Advantageously, the leakage current is measured from the differential power supply current, and the additional resistance is estimated as a function of the leakage current and of the current flowing to the ground.

The resistance of the ground connection and the additional resistance can be estimated by means of a table having resistance values for the ground connection, values of additional resistance and values of current flowing to the ground corresponding to said resistance values for the ground connection and to said values of additional resistance.

Furthermore, a sinusoidal voltage can be generated through the resistance of the ground connection.

It is possible to prohibit the use of the electrical apparatus as a function of the estimate of the resistance of the ground connection.

Advantageously, the use of the electrical apparatus is prohibited if the resistance of the ground connection is higher than the additional resistance.

Other advantages and features of the invention will become apparent on studying the following description, given by way of nonlimiting example and illustrated by the appended drawings, in which.

Figure 1:
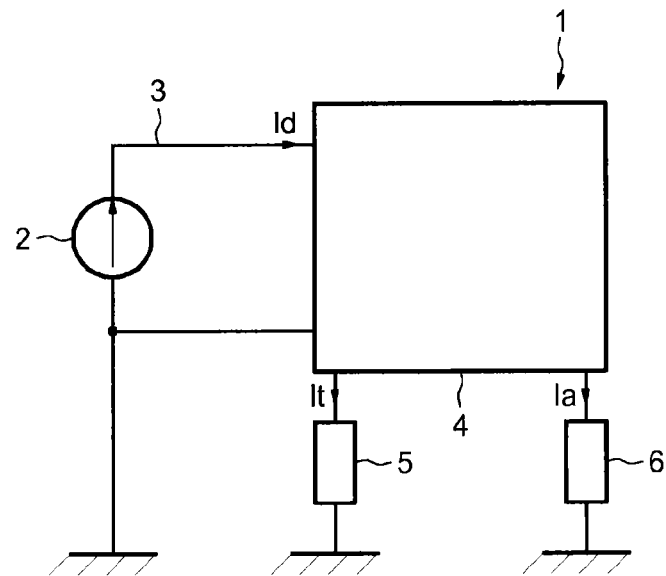
FIG. 1 illustrates an electrical apparatus connected to a power supply system.

FIG. 1 shows an electrical apparatus 1 connected to a voltage source 2, for example a single-phase or three-phase power supply system. The electrical apparatus 1 may be a battery charger for an electric or hybrid traction motor vehicle, for example. The electrical apparatus 1 is connected to the voltage source 2 by an electrical connection 3, which way comprise a plurality of phases and possibly a neutral connection.

The electrical apparatus 1 can be connected to the ground, for example by its electrical chassis 4. In the figure the resistance of the ground connection is represented by the resistance 5.

In the illustrated example, another object is in contact with the electrical chassis 4, and forms a ground connection in parallel with that of the ground connection through the resistance 5, the additional ground connection being represented by the additional resistance 6.

The electrical apparatus 1 is powered by a differential current Id, which notably makes it possible to determine the leakage current. This leakage current can flow to the ground through the resistance of the ground connection 5 and/or the additional resistance 6. Thus, the leakage current forms a current It flowing through the resistance 5 and a current Ia flowing through the additional resistance 6. If the resistance of the ground connection is too high, the leakage current is at least partly redirected to the additional resistance 6 by the current Ia.

Figure 2:
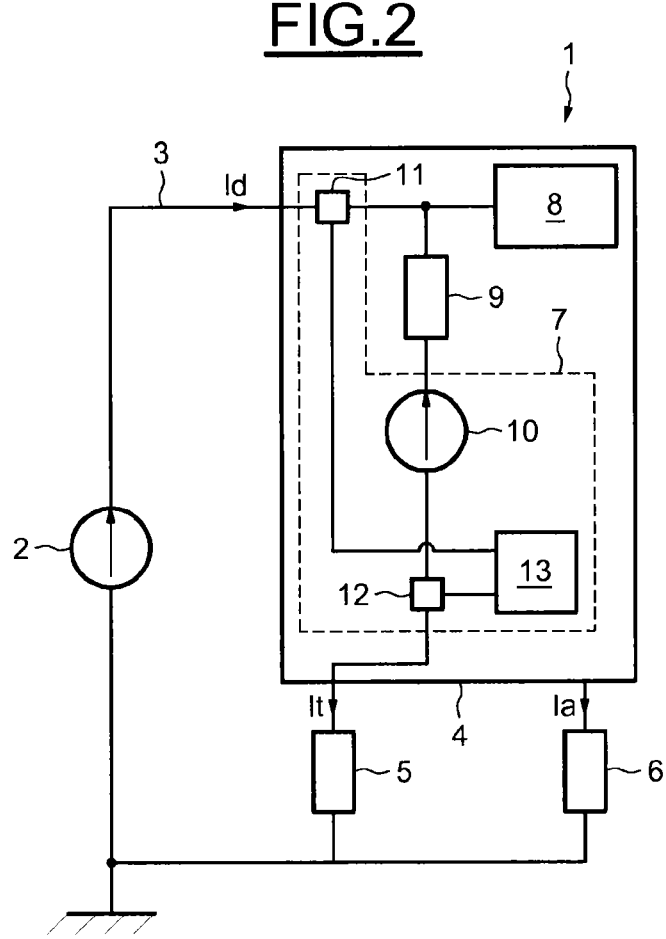
FIG. 2 illustrates an embodiment of a device according to the invention.

FIG. 2 shows an electrical apparatus 1 equipped with a device for estimating the resistance of the ground connection 7, according to an embodiment of the invention.

The electrical apparatus 1 comprises a main element 8, arranged in the electrical chassis 4, and connected to a power supply system by the connection 3. Conventionally, an electromagnetic compatibility filter 9 may be arranged at the input of the electrical apparatus 1, before the main element 8.

A device 7 notably comprising a voltage generator 10 is arranged between the input impedance of the electromagnetic compatibility filter 9 and the ground, through the resistance of the ground connection 5.

Means 11 for measuring the leakage current are arranged on the connection 3. These measurement means 11 may comprise a toroidal coil traversed by the phase and neutral wires, so as to obtain the value of the leakage current in the conventional manner. Means 12 for measuring the current It flowing to the ground can also be arranged after the voltage generator 10 and before the ground connection via the resistance of the ground connection 5. The leakage current is thus measured according to the prior art, for example: a current-measuring toroid via which the supply phases pass into the core. The leakages thus measured are the sum of the current injected into the ground connection resistance 5 and that passing into the additional resistance 6. This leakage current measurement makes it possible to complete the measurement of current in the connection resistance 5, and thus to evaluate the ratio of the connection resistance 5 to the additional resistance 6 by using table 2, cited as an example.

This impedance ratio makes it possible, in addition to measuring the current alone, to define a criterion for authorization of use of the electrical apparatus: for example if charging is not authorized below 5 mA, table 1, prohibited for the pair (10, 10) and (100, 100). On the other hand, use is nevertheless permitted for the pair (10, 10) if the ground quality is good: the second table makes it possible to distinguish this pair to authorize use of the apparatus.

The means for measuring the leakage current and the means for measuring the current flowing to the ground are connected to calculating means 13. These calculating means can estimate the resistance of the ground connection as well as the additional resistance, as a function of the leakage current and of the current It flowing to the ground. The calculating means 13 can notably contain a table having resistance values for the ground connection 5, values of additional resistance 6 and values of current It flowing to the ground corresponding to said values of resistance for the ground connection 5 and of additional resistance 6.

It will be noted that the current Ia flowing through the additional resistance 6 is obtained by calculating the difference between the leakage current and the current It flowing to the ground.

Figure 3:
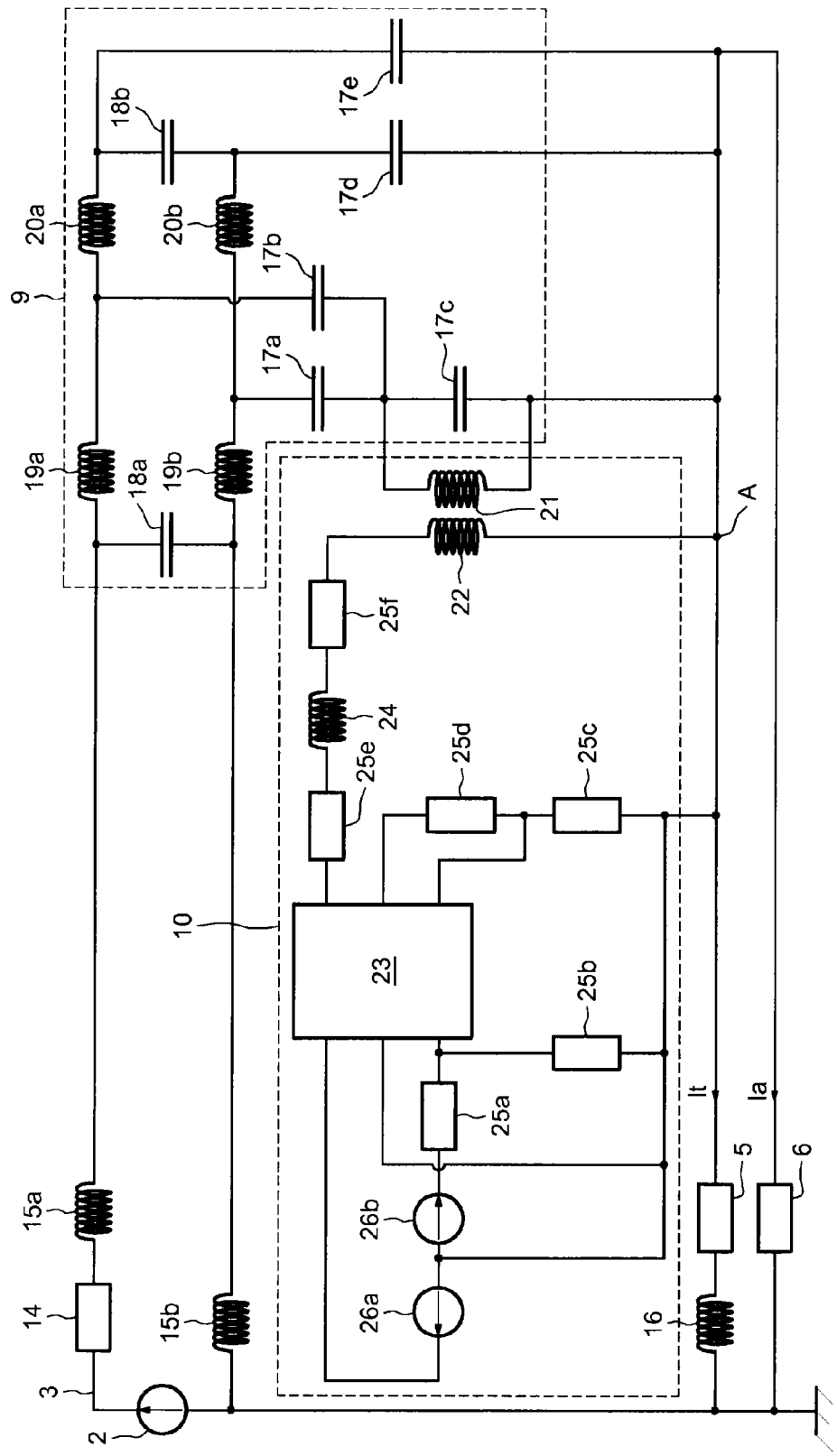
FIG. 3 illustrates an embodiment of a device according to the invention connected to an electromagnetic compatibility filter.

FIG. 3 is a detailed illustration of an exemplary embodiment of the voltage generator 10 connected to the input impedance of the electromagnetic compatibility filter 9. The connection 3 here comprises a resistance 14 and two inductances 15a and 15b because of the cabling used for the connection to the power supply system. Moreover, the connection 3 only contains one phase in the embodiment in FIG. 3. The ground connection also comprises an inductance 16 because of the cabling used, arranged in series with the resistance 5.

The electromagnetic compatibility filter 9 conventionally comprises a plurality of capacitances and inductances. The electromagnetic compatibility filter 9 notably comprises common-mode capacitances 17a, 17b, 17c, 17d and 17e, differential-mode capacitances 18a and 18b, common-mode inductances 19a and 19b and differential-mode inductances 20a and 20b.

The voltage generator 10 notably comprises a primary winding 21 of a transformer arranged in parallel with the common-mode capacitance 17c, and a secondary winding 22 intended to power a voltage-controlled oscillator 23. An inductance 24 is arranged in series between the voltage-controlled oscillator 23 and the secondary winding 22, and makes it possible to inject a sinusoidal current into the ground.

A certain number of resistances 25a, 25b, 25c, 25d, 25e and 25f are used to control the oscillator 23, as well as two voltage generators 26a and 26b.

The voltage generator 10 can thus use the common-mode capacitance 17c to cause a current to flow to the ground from the point A, and to loop this current back to the phases by means of the common-mode capacitances 17a and 17b.

The current It flowing to the ground is measured, as can be the leakage current, and the calculating means 13 then estimate, for example by means of a table, the values of the resistance of the ground connection 5 and of the additional resistance 6.

By way of example, it is possible to measure values of the current flowing to the ground in milliamperes in a calibration step, so as to obtain the following table:

| Current flowing to the ground in milliamperes | Resistance of the ground connection in ohms | | | | |
|---|---|---|---|---|---|
|  | 10 | 100 | 1000 | 5000 | 100 000 |
| Additional resistance in ohms  10 | 5 | 1 | 0.01 | 0.02 | 0 |
| 100 | 9 | 3.3 | 0.5 | 0.1 | 0 |
| 1000 | 9 | 5 | 0.8 | 0.2 | 0.01 |
| 10 000 | 9 | 5.1 | 1 | 0.2 | 0.01 |
| 100 000 | 9 | 5.2 | 1 | 0.2 | 0.02 |

Thus, the calculating means can estimate the resistance of the ground connection and possibly the additional resistance as a function of the current flowing to the ground. It will be noted that the current flowing to the ground is larger for good-quality ground connections.

The calculating means can also contain other tables, for example a table of the leakage current, or a table comprising the ratio of the leakage current to the current flowing to the ground. By way of example, the following table is obtained:

| Ratio of the leakage current to the current flowing to the ground | Resistance of the ground connection in ohms | | | | |
|---|---|---|---|---|---|
|  | 10 | 100 | 1000 | 5000 | 100 000 |
| Additional resistance in ohms  10 | 0.5 | 0.153 | 0.001 | 0.002 | 0 |
| 100 | 1 | 0.471 | 0.5 | 0.018 | 0 |
| 1000 | 1 | 0.909 | 0.8 | 0.02 | 0.01 |
| 10 000 | 1 | 0.962 | 1 | 0.667 | 0.1 |
| 100 000 | 1 | 1 | 1 | 1 | 1 |

Thus, a ratio equal to 1 corresponds to a quality ground connection, in which all the leakage current flows to the ground via the ground connection and not via the additional resistance.

Advantageously, the calculating means are connected to means for prohibiting the use of the electrical apparatus, not illustrated in the figures, making it possible to prevent the operation of the electrical apparatus when the connection is not of good quality.

For example, in the case of a charger for an electric motor vehicle, it will be possible to prevent charging of the vehicle if the ground connection is of poor quality, and thus to protect the users against possible touch currents.

Charging may, however, be authorized for a poor ground connection if the additional resistance allows the current to flow to the ground and is known.

It will be noted that it is possible to implement the estimation of the quality of the ground connection in a continuous or dynamic manner, so as to take into account modifications to the additional resistance.

It should be noted that in this embodiment of the invention the power supply system 2 is connected to the ground on the transformer side. In other embodiments of the invention, the system is of IT type (supply system insulated from the ground), for example, and there will also be an evaluation of the ground connection resistance 5 by the measuring device.

The aim of the invention is not in fact to measure the ground connection resistance 5, but to evaluate its order of magnitude with respect to the additional resistance 6. This can be achieved by the measurement of the current 12 and the calculator 13.

On a good ground (0 ohm), the injected current is known since the current generator is dimensioned with a known value and tolerance, as in table 1 (9 mA), for example. A poor 1000 ohm ground (system in IT configuration, for example) will cause the injected current to fall to 1 mA. A poor 10 000 ohm ground will cause the current to fall to 0.02 mA—a value representative of a ground connector not connected to the ground.

Moreover, the measured current also makes it possible to evaluate a parallel ground not connected by the supply connector: a 100 ohm ground with a parallel ground of 100 ohms will cause the current to fall to 3.3 mA.

It is therefore possible to evaluate good ground connectors (up to 100 ohms) as well as an evaluation of a parallel ground connector not going through the ground connector of the supply voltage connector of the device.

The invention claimed is:

1. A device for estimating a first resistance of a ground connection for an electrical apparatus when the electrical apparatus is connected to a power supply system and is also connected to the ground by a second resistance, the electrical apparatus including at least one input impedance, the estimating device comprising:
a voltage generator including means for connecting to the input impedance and means for connecting to the ground connection;
means for measuring current flowing to the ground through the first resistance of the ground connection when the means for connecting to the input impedance and to the ground connection are activated; and
calculating means configured to obtain an order of magnitude for the first resistance of the ground connection, as a function of the current flowing to the ground, the obtained order of magnitude being with respect to a value of the second resistance.

2. The device as claimed in claim 1, further comprising means for measuring leakage current from a differential supply current for the electrical apparatus, and wherein the calculating means is configured to estimate an additional resistance as a function of the leakage current and of the current flowing to the ground.

3. The device as claimed in claim 2, wherein the calculating means comprises a table including resistance values for the ground connection, values of additional resistance, and values of current flowing to the ground corresponding to the resistance values for the ground connection and to values of the additional resistance.

4. The device as claimed in claim 1, wherein the input impedance is an input impedance of an electromagnetic compatibility filter.

5. The device as claimed in claim 1, wherein the voltage generator is a voltage-controlled oscillator.

6. The device as claimed in claim 1, further comprising means for prohibiting use of the electrical apparatus as a function of the order of magnitude of the first resistance of the ground connection.

7. The device as claimed in claim 1, wherein the electrical apparatus is a battery charger for an electric or hybrid traction motor vehicle.

8. A method for estimating a first resistance of a ground connection for an electrical apparatus when the electrical apparatus is connected to a power supply system and is also connected to the ground by a second resistance, the estimation method comprising:

generating a current between an input impedance of the electrical apparatus and the first resistance of the ground connection;

measuring current flowing to the ground through the first resistance of the ground connection to obtain an order of magnitude for the resistance of the ground connection with respect to a value of the additional resistance; and calculating an order of magnitude for the first resistance of the ground connection, as a function of the current flowing to the ground, the calculated order of magnitude being with respect to a value of the second resistance.

9. The method as claimed in claim 8, further comprising measuring a leakage current from a differential power supply current, and the second resistance is estimated as a function of the leakage current and of the current flowing to the ground.

10. The method as claimed in claim 9, wherein the first resistance of the ground connection and the second resistance are estimated by a table having resistance values for the ground connection, values of additional resistance, and values of current flowing to the ground corresponding to the resistance values for the ground connection and to values of the additional resistance.

11. The method as claimed in claim 8, wherein a sinusoidal current is generated through the first resistance of the ground connection.

12. The method as claimed in claim 8, wherein use of the electrical apparatus is prohibited as a function of the order of magnitude of the first resistance of the ground connection.

13. The method as claimed in claim 12, wherein use of the electrical apparatus is prohibited if the first resistance of the ground connection is higher than the second resistance.

14. A device for estimating a first resistance of a ground connection for an electrical apparatus when the electrical apparatus is connected to a power supply system and is also connected to the ground by a second resistance, the electrical apparatus including at least one input impedance, the estimating device comprising:

a voltage generator connected to the input impedance and connected to the ground connection;

circuitry configured to measure current flowing to the ground through the first resistance of the ground connection; and processing circuitry configured to calculate an order of magnitude for the first resistance of the ground connection, as a function of the current flowing to the ground, the calculated order of magnitude being with respect to a value of the second resistance.

* * * * *